US005648578A

United States Patent [19]
Layman et al.

[11] Patent Number: 5,648,578
[45] Date of Patent: Jul. 15, 1997

[54] PREPARATION OF POLYALKYLATED CYCLOPENTADIENES FROM ISOBORNYL CARBOXYLATES

[75] Inventors: William J. Layman, Orangeburg, S.C.; Gene C. Robinson, Baton Rouge, La.

[73] Assignee: Albemarle Corporation, Richmond, Va.

[21] Appl. No.: 428,471

[22] Filed: Apr. 26, 1995

[51] Int. Cl.⁶ .............................. C07C 13/28; C07C 1/20
[52] U.S. Cl. .............................................. 585/352; 585/357
[58] Field of Search ............................... 585/352, 357

[56] References Cited

U.S. PATENT DOCUMENTS

| | | | |
|---|---|---|---|
| 4,547,603 | 10/1985 | Rajan | 585/375 |
| 4,814,532 | 3/1989 | Yoshida et al. | 585/357 |
| 5,329,056 | 7/1994 | Belmont | 585/358 |

OTHER PUBLICATIONS

De Haan, J. W., et al., Recuel, 1968, 87, 289–297 no month available.
Mironov, V.A., et al., Russ. Chem. Rev., 1981, 50, 666–679 no month avialable.

*Primary Examiner*—Glenn A. Caldarola
*Assistant Examiner*—Elizabeth D. Wood
*Attorney, Agent, or Firm*—Philip M. Pippenger

[57] ABSTRACT

A process for preparing tetraalkylated cyclopentadienes comprises (a) pyrolyzing an isobornyl carboxylate so as to form a mixture of 1,2,3- and 1,2,4-trimethylcyclopentadienes, (b) alkylating said mixture with an alkylating agent so as to form a mixture of alkyltrimethylcyclopentadiene isomers including 1,2,3,4-alkyltrimethylcyclopentadiene and, (c) thermally isomerizing the mixture of isomers obtained in step (b) so as to increase the proportion of 1,2,3,4-alkyltrimethylcyclopentadiene in said mixture of isomers.

10 Claims, No Drawings

PREPARATION OF POLYALKYLATED CYCLOPENTADIENES FROM ISOBORNYL CARBOXYLATES

FIELD OF THE INVENTION

This invention relates generally to the preparation of polyalkylated cyclopentadienes and more specifically to a process for preparing tetraalkylated cyclopentadienes, such as 1,2,3,4-tetramethylcyclopentadiene, from isobornyl carboxylates, such as isobornyl acetate.

BACKGROUND

Polyalkylsubstituted cyclopentadienes are useful as monomers and in forming metallocenes of transition metals. Such metallocenes are useful components of olefin polymerization catalysts, as is known in the art. U.S. Pat. No. 5,329,056 discloses the preparation of substituted cyclopentadienes, including 1,2,3,4-tetramethylcyclopentadienes starting with a vinyl ketone and a vinyl halide. The pyrolysis of isobornyl acetate to yield mixtures containing 1,2,3- and 1,2,4-trimethylcyclopentadienes has been reported by De Haan et al., Rec. Trav. Chim. (1968), 87, 289–297. The pyrolysis of 1,4,5,5-tetramethylcyclopentadiene, prepared in low yields from methylcyclopentadiene to form 1,2,3,4-tetramethylcyclopentadiene has been reviewed in Mironov et al., Russ. Chem. Rev. (1981), 50, 666–679.

SUMMARY OF THE INVENTION

This invention is intended to provide a more economic process for preparing tetraalkylated cyclopentadienes which can start with isobornyl acetate, which is inexpensive and readily available.

In accordance with this invention there is provided a process for the preparation of tetraalkylated cyclopentadienes, said process comprising the steps of (a) pyrolyzing a isobornyl carboxylate so as to form a mixture which includes 1,2,3- and 1,2,4-trimethylcyclopentadienes, (b) alkylating said mixture with an alkylating agent so as to form a mixture of alkyltrimethylcyclopentadiene isomers, including 1,2,3,4-alkyltrimethylcyclopentadiene and geminally substituted alkyltrimethylcyclopentadienes and (c) thermally isomerizing the mixture of isomers obtained in step (b) so as to increase the proportion of 1,2,3,4-alkyltrimethylcyclopentadiene in said mixture of isomers.

DESCRIPTION OF PREFERRED EMBODIMENTS

The first step of the process pyrolyzes an isobornyl carboxylate to form a mixture of trimethylcyclopentadienes. Isobornyl acetate is the preferred starting material because it provides high yields and is commercially available. However, isobornyl esters of any $C_2$ to $C_{18}$ alkyl, aryl, alkaryl and arylalkyl carboxylic acid could be used, for example, the isobornyl esters of propionic, butyric, valeric, caproic, stearic, benzoic, o-toluic, α-toluic, and naphthoic acids.

Isobornyl acetate is commercially available. The isobornyl acetate can be pyrolyzed at temperatures of from about 400° to 500° C. such as by feeding it to the upper end of a heated tube, either neat or preferably in combination with from about 5 to 70 volume percent of an inert hydrocarbon solvent such as pentane. A flow of an inert gas, such as is provided by a stream of nitrogen flow rate (12–24 sccm), can be used to vaporize the feed and move it down through the reactor tube. The pyrolyzate is then condensed such as by a glycol cooled condenser or a cold trap and collected. The conversion is >95% and the yield of 1,2,3- and 1,2,4-trimethylcyclopentadienes is as high as 82%. After the crude product is washed such as with water and saturated sodium bicarbonate, a more concentrated 1,2,3- and 1,2,4-trimethylcyclopentadiene cut from the reaction mixture is obtained by fractional distillation (temp. 38° to 40° C.) at reduced pressure (12 to 17 mm Hg).

The distilled trimethylcyclopentadiene fraction from the pyrolysis is then alkylated with a suitable alkylating agent to form primarily tetrasubstituted cyclopentadienes. This selectivity of the alkylation is believed to result from the formation of a large quantity of cyclopentadienes having geminal alkyl groups, e.g., the 1,4,5,5-, 1,2,3,3-, 1,2,4,4-tetramethylcyclopentadienes. The geminal substitution acts as a protecting group and prevents further alkylation by blocking further formation of a cyclopentadiene anion intermediate. These geminal alkyl substituted cyclopentadienes are converted to the desired 1,2,3,4-alkyl substituted cyclopentadiene product by thermal isomerization in the final step of the process.

A variety of alkylation reagents can be used, for example, alkylhalides and sulfates in which the alkyl groups contain from about 1 to 8 carbons in conjunction with a variety of metalating agents, for example sodium metal, lithium metal and potassium metal. Also alkyl lithium and other basic organometallic species can be used. A preferred method for forming tetramethyl-substituted cyclopentadienes is to use dimethylsulfate or methyl chloride in combination with a strong base, e.g. sodium amide in liquid ammonia or aqueous caustic with trialkylammonium chloride. Mole ratios of alkylating agent to cyclopentadiene reactant of from about 0.80 to 12 mole per mole of cyclopentadiene can be used and, preferably, from about 0.9 to 1.0 mole per mole of cyclopentadiene. The product is a complex mixture of isomers including the geminally substituted compounds as well as the desired 1,2,3,4-tetrasubstituted product. It has been found that the amount of the desired product in this complex mixture can be increased by thermal isomerization which converts the geminally substituted isomers to the 1,2,3,4-isomer in conversions of up to about 75%. A pyrolysis tube reactor as is used for step 1 can be employed for the thermal isomerization. Suitable temperatures range from about 400° to 500° C. and the isomer mixture is preferably mixed with up to about 50 volume percent of an inert solvent and pyrolyzed in a stream of inert gas such as nitrogen. Flow rates generally range from about 10 to 20 sccm. In order to prevent charring of the product, polar impurities, such as acidic artifacts which may be formed in the alkylation reaction from the dimethylsulfate, should be removed. For example, a pentane solution of the isomer mixture can be filtered through a plug of silica gel. The pyrolyzate can be collected, concentrated under reduced pressure, and the product distilled at reduced pressure (0.2 to 0.15 mm Hg) and temperatures of from about 20° to 25° C. The process is further illustrated by, but is not intended to be limited to, the following examples.

EXAMPLE 1A

Pyrolysis of isobornyl acetate: Isobornyl acetate, 115 g (0.58 mole) is dissolved in 115 mL of pentane. The solution is pumped at a rate of 0.77 mL/min into the upper end of a tubular pyrolysis reactor heated to 460° C. Pyrolysis is conducted under a stream of nitrogen (12.5 mL/min). The pyrolyzate is collected and washed with water and saturated sodium bicarbonate solution. The product mixture is obtained by fractional distillation at reduced pressure. A 47 g (65% yield) fraction has a GC assay of 87% of a mixture of 1,2,3- and 1,2,4-trimethylcyclopentadienes.

EXAMPLE 1B

Methylation of 1,2,3- and 1,2,4-trimethylcyclopentadiene: An oven-dried, 1000 mL, 4-neck round bottom flask is equipped with a dry-ice condenser, addition funnel, and rubber septum. The flask is charged with 500 mL of liquid ammonia. Sodium amide is generated from 4.3 g of sodium metal and a catalytic amount of ferric nitrate. The neat trimethylcyclopentadiene mixture, (18 g, 0.169 mole), is added to the sodium amide solution in portions. Dimethyl sulfate, 0.189 mole, is added dropwise to the solution. Anhydrous ether, 115 mL is then added to the reaction mixture which is left to stir for two hours. The reaction is quenched with 50 mL of water and the excess ammonia is allowed to evaporate. The residue is partitioned between water and ether. The ether phase is collected, dried over magnesium sulfate, filtered and concentrated to 20.5 g of an oil. GC analysis of the oil shows that it is a complex mixture of polymethylated cyclopentadienes.

EXAMPLE 1C

Thermal isomerization of tetramethylcyclopentadienes: The oil from Example 1B is dissolved in 100 g of pentane and filtered through a plug of silica gel to remove acidic impurities. The pentane solution is then pumped to the pyrolysis reactor at a rate of 1.0 mL/min. The material is pyrolyzed at 410° C. in a stream of nitrogen with a flow rate of 12.5 mL/min. The pyrolyzate is collected and concentrated under reduced pressure to yield 17 g of an oil. The oil is distilled at 25° C. at 0.15 mm Hg into a dry-ice-cooled receiving flask to yield 16.1 g of a yellow oil. The yellow color dissipates on standing to leave a clear colorless oil. GC analysis of the oil shows the following composition: 63% 1,2,3,4-tetramethylcyclopentadiene, 12% trimethylcyclopentadienes, 9% other tetramethylcyclopentadienes and 10% 1,2,3,4,5-pentamethylcyclopentadiene.

The following examples illustrate alternative alkylation procedures.

EXAMPLE 2

Sodium (8.94 g, 0.39 g-atom) is added to dry bis(2-methoxyethyl)ether (210 mL. nitrogen atmosphere) contained in a three-necked flask filled with a stirrer, a condenser, and an addition funnel. The bis(2-methoxyethyl) ether is heated to 98°–105° C. to melt the sodium which is then dispersed with the stirrer. To the dispersion is slowly added mixed trimethylcyclopentadienes (52 g, 0.48 mole). Then methyl chloride (27.8 g, 0.55 mole) is slowly added at 18°–32° C. as it is consumed. The sodium chloride in the resultant slurry is separated by filtration and the product mixture is subjected to fractional distillation. The mixed tetramethylcyclopentadiene fraction is subjected to pyrolysis as described in Example 1C to obtain 1,2,3,4-tetramethylcyclopentadiene.

EXAMPLE 3

A stainless steel autoclave is charged with 50% sodium hydroxide (57 g, 0.7 mole), 80 percent tri-n-butylmethylammonium chloride (1 g, 0.0034 mole), and trimethylcyclopentadiene (mixed isomers, 32.4 g, 0.3 mole). Methyl chloride (15.7 g, 0.31 mole) is added at 60 psi and 25°–30° C. After reaction completion, the organic product phase is separated from the lower aqueous phase containing excess base and sodium chloride slurry. The mixture of crude tetramethylcyclopentadienes is subject to pyrolysis as described in Example 1C to obtain 1,2,3,4-tetramethylcyclopentadiene.

What is claimed is:

1. A process for the preparation of tetraalkylated cyclopentadienes, said process comprising the steps of (a) pyrolyzing an a isobornyl carboxylate so as to form a mixture of 1,2,3- and 1,2,4-trimethylcyclopentadienes, (b) alkylating said mixture with an alkylating agent so as to form a mixture of alkyltrimethylcyclopentadiene isomers including 1,2,3,4-alkyltrimethylcyclopentadiene and (c) thermally isomerizing the mixture of isomers obtained in step (b) so as to increase the proportion of 1,2,3,4-alkyltrimethylcyclopentadiene in said mixture of isomers.

2. The process of claim 2 wherein said isobornyl carboxylate is isobornyl acetate.

3. The process of claim 3 wherein said alkylating agent is a methylating agent such that the product is 1,2,3,4-tetramethylcyclopentadiene.

4. The process of claim 3 wherein the methylating agent is dimethyl sulfate or methyl chloride.

5. The process of claim 1 wherein polar impurities are removed from said mixture of isomers obtained in step (b) prior to thermal isomerization.

6. The process of claim 1 wherein isobornyl acetate is mixed with an inert hydrocarbon solvent and fed to a heated pyrolysis tube where it is vaporized and moved through the tube by a flow of an inert carrier gas.

7. The process of claim 1 wherein the pyrolysis temperature is from about 400° to 500° C.

8. The process of claim 1 wherein the thermal isomerization temperature is from about 400° to 500° C.

9. The process of claim 1 wherein the mixture of alkyltrimethylcyclopentadiene isomers is mixed with an inert hydrocarbon solvent and fed to a heated pyrolysis tube where it is vaporized and moved through the tube by a flow of an inert carrier gas.

10. The process of claim 1 wherein said alkylation is carried out under basic conditions.

* * * * *